United States Patent [19]

Lipatov et al.

[11] Patent Number: 4,957,499

[45] Date of Patent: Sep. 18, 1990

[54] SURGICAL SUTURING INSTRUMENT

[76] Inventors: Viktor A. Lipatov, ulitsa Profsojuznaya, 91, korpus 3, kv.27; Igor A. Guskov, ulitsa Tulinskaya, 10, Korpus I, kv.80; Nikolai N. Kanshin, ulitsa M. Filevskaya, 68, kv.10, all of Moscow, U.S.S.R.

[21] Appl. No.: 332,452

[22] PCT Filed: Jun. 27, 1988

[86] PCT No.: PCT/SU88/00020

§ 371 Date: Mar. 9, 1989

§ 102(e) Date: Mar. 9, 1989

[87] PCT Pub. No.: WO89/00406

PCT Pub. Date: Jan. 26, 1989

[30] Foreign Application Priority Data

Jul. 14, 1987 [SU] U.S.S.R. .............................. 4268008

[51] Int. Cl.$^5$ .............................................. A61B 17/00
[52] U.S. Cl. ..................................... 606/153; 227/180
[58] Field of Search ......................... 606/153; 227/180

[56] References Cited

U.S. PATENT DOCUMENTS

| | | | |
|---|---|---|---|
| 4,289,133 | 9/1981 | Rothfuss | 227/180 |
| 4,476,863 | 10/1984 | Kanshin et al. | 606/153 |
| 4,505,272 | 3/1985 | Utyamysher et al. | 227/180 |
| 4,567,891 | 2/1986 | Kanshin et al. | 606/153 |

*Primary Examiner*—Randall L. Green
*Assistant Examiner*—Gary Jackson
*Attorney, Agent, or Firm*—Fleit, Jacobson, Cohn, Price, Holman & Stern

[57] ABSTRACT

A surgical suturing instrument for establishing circular compression anastomoses in the organs of the digestive tract comprises a rod (2) accommodated in a hollow body (1) coaxially therewith and having a stationary fixed connecting ring (13), a hollow cylindrical knife (3) made fast of a hollow tube (4) which is accommodated in the hollow body coaxially therewith the rod (2) passing inside the hollow tube, a needle arrangement (5) accommodated in the hollow body and having a first ring-shaped element (6) provided with a plurality of holes (8), and a second ring-shaped element (7) coaxial with the first one and carrying a plurality of needles (9) held thereto and adapted to pass through the connecting ring (13) in the course of anastomosing. The ring-shaped element (7) rests upon a pusher (19) having a hollow chamfer (20) and a stop (21) which is adapted to interact with a stop (22) of the hollow body (1). The instrument comprises also a split bush (23) located on the hollow tube (4) and having a taper collar (24) adapted to engage the hollow chamfer (20) of the pusher (19), and a retainer (25) of the split bush (23) located on the hollow tube (4).

13 Claims, 5 Drawing Sheets

SURGICAL SUTURING INSTRUMENT

TECHNICAL FIELD

The invention relates generally to surgical appliances and is concerned more specifically with surgical suturing instruments.

PRIOR ART

Known in the present state of the art is a surgical instrument adapted for establishing anastomoses with the aid of a staple suture applied to such tubular organs as those of the digestive canal. The instrument comprises a thrust die or matrix, a cylindrical body having at least one ring or surgical staples, a mechanism actuating the surgical staples, and a cylindrical scalpel, with the aid of which mechanism the staples make their way through tubular organs and get united at the surface of the thrust dies, while the scalpel cuts off an excess protion of the tubular organs being operated upon (GB, A, 2,133,735).

The aforesaid known instrument makes use of staples which remain for a prolonged time or permanently in the patient's organism. Such staples fail to establish a staunch suture which might inflict morbid postoperative events.

Another prior-art suturing instrument is known, adapted to establish circular compression anastomoses in the organs of the digestive tract. The instrument comprises a needle arrangement having a first ring-shaped element provided with a plurality of holes and a second ring-shaped element carrying a plurality of needles fixed in position thereon and equal in number to said holes in the first ring-shaped element, each of said needles corresponding to one of the aforesaid holes and at least part of said needles have a locking cone at the free end thereof. Both of the ring-shaped elements are coaxially arranged and enclosed in a hollow body, wherein a rod is accommodated, coaxial with the ring-shaped elements, said rod having at one of its ends a fixed connecting ring set with the aid of a round nut. When establishing an anastomosis the needles are passed through the connecting ring and some of them are fixed therein with the locking cones.

The instrument comprises also a cylindrical knife whose inside diameter is equal to the maximum nut diameter and which is secured on a hollow tube accommodated in the housing, a rod being coaxially accommodated in said tube. The cylindrical knife has a mechanical actuator adapted to interact with the hollow tube and comprising a movable handle rotatably mounted with respect to the body and provided with a lever which is to interact with the slots in the hollow tube (PCT/SU 79/00049).

The ring-shaped elements of the needle arrangement and the connecting ring are made of elastic or plastic materials which must be biologically inert, nontoxic and noncancerogenic.

In order to establish an end-to end anastomosis the instrument is to be placed inside the tubular organ operated upon. The ends of the tissue of the organs operated upon are fixed on the rod with the aid of purse-string sutures. Once the working members of the apparatus have been brought together and the needle arrangement has been approximated to the connecting ring, the tissues are also approximated till contacting with their exterior serous surfaces, whereupon the movable handle is depressed to actuate the hollow tube and the cylindrical knife to move concurrently with the travel of the needle arrangement, whereby the needles of the second ring-shaped element are urged to pierce the tissues, and the stationary fixed connecting ring is held thereto by means of the needles with the locking cones. Upon further advancing the cylindrical knife cuts off the excess tissues and cuts through the stationary fixed ring, thus establishing an anastomotic opening through which is withdrawn the rod end fitted with the round nut. The tissue confined between the needle arrangement and the connecting ring is compressed, thus ensuring a staunch suture, followed by reunion of the tissues and, 7 to 10 days after surgery, the needle arrangement and the connecting rign which compress the tissue involved are expelled into the interior of the hollow organ operated upon. Afterwards both the needle arrangement and the connecting ring are discharged through the natural way of elimination.

A disadvantage inherent in the known instrument resides in injury to the living tissues being sutured at the instant of approximation of the connecting ring and the needle arrangement and suturing when the cylindrical knife cuts off the surplus tissues being stitched together and starts cutting through the connecting ring. As a result, the needles that have already been fixed in the connecting ring by the locking cones, keep sinking into the ring till the latter is completely cut through by the knife, thus overcompressing the tissue involved.

Since cutting the connecting ring through by the knife occurs simultaneously with advancing of the needles through said ring the latter gets deformed, which results in an increased suturing effort and additional injury to the living tissues being sutured.

DISCLOSURE OF THE INVENTION

It is an object of the invention to provide a surgical suturing instrument which, while having a single mechanical actuator, would make it possible to separate in time the processes of piercing the tissues being sutured and of cutting the central opening in living tissues owing to a modified interaction of the cylindrical knife and the needle arrangement.

The foregoing object is accomplished due to the fact that a surgical suturing instrument for establishing circular compression anastomoses in the organs of the digestive tract, comprising a needle arrangement accommodated in a hollow body and having a first ring-shaped element with a plurality of holes, and a second ring-shaped element coaxial with the first one and carrying a number of needles fixed in position thereon, each of said needles corresponding to one of the holes in the first ring-shaped element, while at least part of said needles have a locking cone at the free end thereof, a rod accommodated in the hollow body, said rod carrying at one of its ends a connecting ring fixed stationary with the aid of a nut, said connecting ring being adapted for the needles to pass through when establishing an anastomosis and those needles which have a locking cone get secured in position in said connecting ring, a hollow cylindrical knife having such an inside diameter that enables the nut to pass freely therethrough, said knife being held to a hollow tube which is arranged coaxially in the hollow body and which accommodates said rod located coaxially therewith, and a mechanical actuator of the hollow cylindrical knife adapted to interact with the hollow tube, according to the invention, has a pusher upon one of whose ends rests the second ring-shaped element of the needle arrangement, while its other end has a hollow chamfer and a stop which is adatped to interact with a stop of the hollow body so as to restrict the travel of the second ring-shaped element in the course of anastomosing, a split bush fitted on the hollow tube and having an outside taper collar adapted to engage the hollow chamfer of the pusher, and a retainer of the split bush located on the hollow tube and accommodated inside the split bush.

To ensure against spontaneous pusher travel the instrument may have a retention device comprising a cylinder-shaped element which is provided with a recess and is located inside the hollow body close to the hollow tube in which a cylindrical recess is made, corresponding to the cylinder-shaped element and a handle provided on the cylinder-shaped element rotatably with respect to the hollow body in order to bring the recess in the cylinder-shaped element in coincidence with the cylindrical recess of the hollow tube, thus letting the hollow tube move and preparing the instrument for suturing.

It is expedient that the retainer of the split bush be shaped as a hollow tube rigidly coupled to the hollow body and arranged coaxially therewith.

The hollow tube serving as the retainer of the split bush may also serve as the casing of the instrument and have a length comparable with the rod length.

The retainer of the split bush may also comprise a bush coaxial with the rod and having a diametral opening, and a supporting element located in the diametral opening of the bush and having its own opening coaxial with the bush and adapted for the rod to pass, said rod having a stop adapted to interact with the supporting element so as to stop the pusher and hence the needle arrangement at the instant when the hollow cylindrical knife cuts through the connecting ring.

It is also expedient that the hollow tube on which the hollow cylindrical knife is secured, be provided with longitudinal slots located on its portion interacting with the bush of the split bush retainer, the slots being adapted for the supporting element to slide with respect to the hollow tube in the course of anastomosing.

The hollow tube carrying the hollow cylindrical knife may serve as the casing of the instrument and have a length comparable with that of the rod.

It is likewise expedient that the hollow body be spring-actuated with respect to the hollow tube carrying the hollow cylindrical knife and be adapted to interact with the bush of the split bush retainer, thus contributing to less overcompression of the tissues being sutured should these be of considerable thickness.

It is favourable that the bush of the split bush retainer be spring-actuated with respect ot the hollow tube on which the hollow cylindrical knife is made fast.

The herein-proposed surgical suturing instrument reduces the degree of traumatic lesion of the living tissues being sutured within the zone of contact during the suturing process.

Provision of a retention device ensures against spontaneous pusher movement when making the instrument ready for suturing.

Provision of a hollow tube with a knife or a hollow retainer bush as a casing renders the construction of the entire instrument simpler and at the same time more convenient in use.

Provision of a spring-actuated housing makes it possible to reduce the degree of injury to the tissues involved should these be of considerable thickness.

Provision of a spring-actuated retainer bush prevents the latter against unlocking

SUMMARY OF THE DRAWINGS

Further objects and advantages of the present invention will hereinafter become apparent from a consideration of a detailed description of some exemplary embodiments thereof with reference to the accompanying drawings, wherein.

PREFERRED EMBODIMENT OF THE INVENTION

Figure 1:
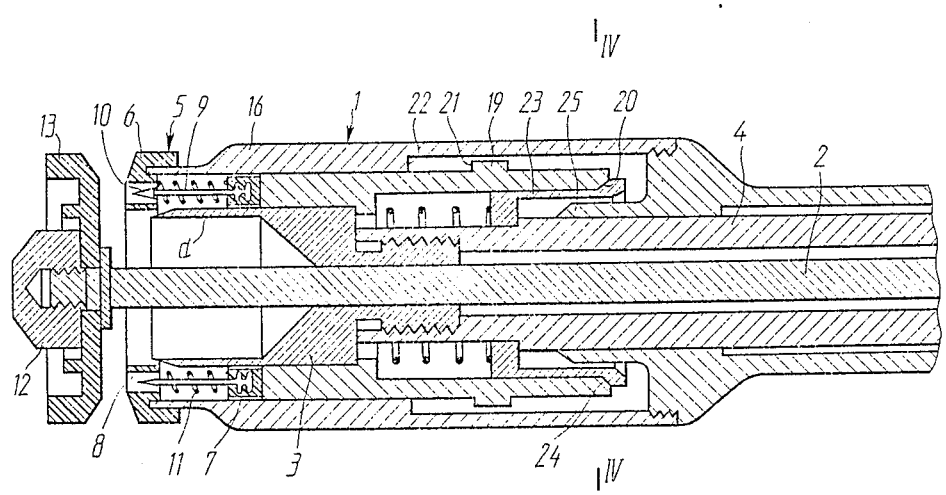
FIG. 1 is a fragmentary longitudinal sectional view of a surgical suturing instrument, according to the invention.

The surgical suturing instrument for establishing circular compression anastomoses in the organs of the digestive tract comprises a hollow body 1 (FIG. 1) which accommodates a rod 2 and a hollow cylindrical knife 3 made fast on a hollow tube 4, both the rod 2 and the hollow cylindrical knife 3 being arranged coaxially with the hollow body 1. A detachable needle arrangement 5 is accommodated in the body 1 coaxially therewith, said needle arrangement comprising coaxial ring-shaped element 6 and 7. A number of holes 8 are made in the ring-shaped element 6 and a number of needles 9 are held to the ring-shaped element 7, each of the needles 9 corresponding to each of the holes 8. Some of the needles 9 but at least three of them have a locking cone 10 at their free end. The ring-shaped element 6 is spring-actuated with respect to the element 7 by means of springs 11 situated round a part of the needles 9.

A connecting ring 13 is held at one end of the rod 2 with the aid of a nut 12, said ring being adapted to join the needle arrangement 5 so as to fix the living tissues being sutured.

The cylindrical knife 3 has an inside diameter 'd' the size of which allows the nut 12 to pass through the interior of the knife 3 after the ring has been cut through.

The hollow tube 4 is arranged in the hollow body 1 coaxially therewith and accommodates the rod 2.

Figure 2:
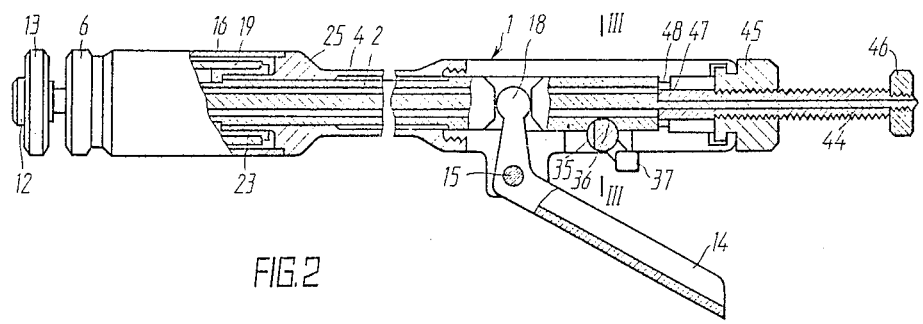
FIG. 2 is a general view, partly in longitudinal section, of the surgical suturing instrument of FIG. 1, according to the invention.
Figure 3:
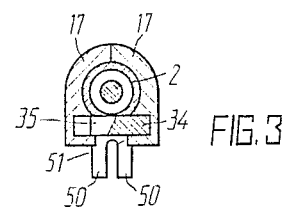
FIG. 3 is a section taken along the line III—III in FIG. 2.

The knife 3 has a mechanical actuator made as a handle 14 (FIG. 2) rotatable round a hinge joint 15 with respect to the body 1 which is constituted by three separable portions 16, 17 (FIG. 3).

The portions 17 of the body 1 are in fact the components of a bush split along its longitudinal axis; they constitute the stationary fixed body 1 at the section when the handle 14 is located. The handle 14 (FIG. 2) has a lever 18 adapted to interact with the tube 4 so as to cause it to travel along with the knife 3.

Figure 4:
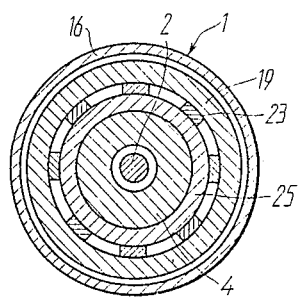
FIG. 4 is a section taken along the line IV—IV in FIG. 1.

The ring-shaped element 7 (FIG. 1) rests upon a pusher 19 (FIGS. 1, 4) having a hollow chamfer 20. The pusher 19 has a stop 21 shaped as a projection and adapted to interact with a stop 22 provided on the inner surface of the body 1 and shaped as a shoulder. Fitted on the hollow tube 4 is a split bush 23 which has an outside taper collar 24 corresponding to the hollow chamfer 20 of the pusher 19.

A retainer is located in the interior of the split bush 23 and on the hollow tube 4. FIG. 1 presents an embodiment of the retainer as a hollow tube 25 rigidly coupled to the hollow body 1. The tube 25 is coaxial with the body 1 and serves as the casing of the entire instrument. Since its length is comparable with the length of the rod 2 the tube 25 encompasses the hollow tube 4 accommodating the rod 2 at the middle portion of the instrument. The tube 25 being the casing of the instrument, it interconnects rigidly the portions 16 and 17.

Figure 5:
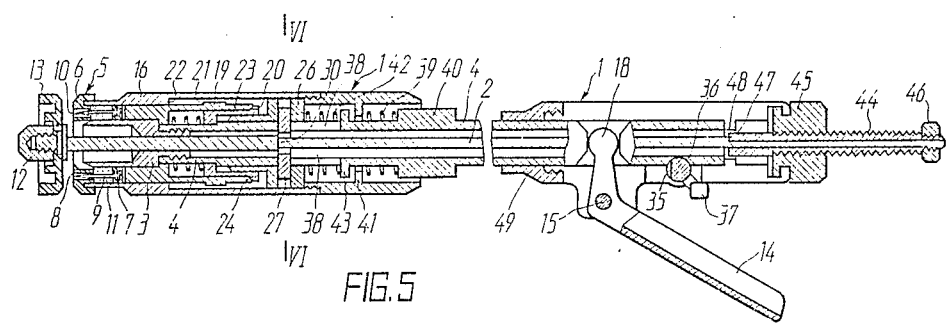
FIG. 5 is a general longitudinal sectional view of an alternative embodiment of the surgical suturing instrument, according to the invention.
Figure 6:
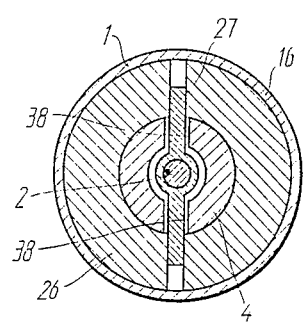
FIG. 6 is a section taken along the line VI—VI in FIG. 5.

FIG. 5 presents an alternative embodiment of the retainer of the split bush 23, which comprises a bush 26 accommodated in the body coaxially with the rod 2, and a supporting element 27 (FIGS. 5, 6) located in a diametral opening 28 of the bush 26. An opening 29 is provided in the element 27 coaxial therewith and with the bush 26 and adapted for the rod 2 to pass.

A stop 30 is provided on the portion of the rod 2 where the supporting element 27 is located, said stop being shaped as a projection. However, the stop 30 can also be made as the end face of the keyway in the rod 2 or else the face of a flat on the rod 2.

The stop 30 is adapted to interact with the element 27 so as to stop the pusher 19 and the needle arrangement 5 at the instant when the knife 3 cuts through the connecting ring 13.

With such an embodiment of the retainer with the bush 26 of the split bush 23 it is the hollow tube 4 (FIG. 5) which serves as the casing of the instrument. In this case the length of the hollow tube 4 is comparable with the length of the rod 2.

Figure 7:
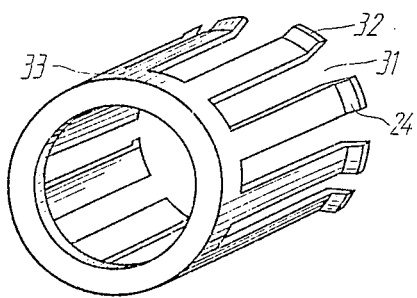
FIG. 7 is a general view of a split bush, according to the invention.

The split bush 23 (FIG. 7) is essentially a hollow cylinder whose side surface is divided, by through slots 31, into a number of prongs 32 united by a nonsplit portion 33 of the cylinder itself. A taper collar 24 is provided at the free end of each prong 32. The number of the prongs 32 depends on the effort to be applied to the needles 9 so as to pierce through the connecting ring 13 and hence on the force of suturing. The instrument comprises also a retention device which ensures against spontaneous movement of the pusher 19 and is provided with a cylinder-shaped element 34 (FIG. 2, 3, 5) interposed between the portions 17 of the body 1 square with the axis of the rod 2. The cylinder-shaped element 34 has a recess 35 corresponding to a cylindrical recess 36 on the portion of the hollow tube 4 close to which the retention device is located. A handle 37 is provided on the cylinder-shaped element 34 which turns the latter so as to bring in coincidence the recesses 35 and 36 at the instant when the hollow tube 4 is unlocked for further travelling.

The hollow tube 4 (FIG. 5) has a number of longitudinal slots 38 on its portion interacting with the bush 26, said slots being adapted for the supporting element 27 to travel with respect to the tube 4 in the course of anastomosing.

The body 1 is actuated with respect to the tube 4 by a spring 39 fitted on the hollow tube 4 between its projection 40 and a projection 41 on the body 1.

The bush 26 of the retainer of the split bush 23 is actuated with respect to the hollow tube 4 by a spring 42 fitted on the hollow tube 4 between its projection 43 and the end of the bush 26.

The knife 3 is thread-fitted on the tube 4.

The rod 2 runs inside a holloow screw 44 engaged with a nut 45 which is rotatably mounted in the portions 17 of the body 1. The free end of the rod 2 has a thread on which a nut 46 is fitted. When the nut 46 rotates the rod 2 is advanced from the screw 44 till its end 47 thrusts against the end of the screw 44 which is kept against rotation due to a nonround slot 48 provided in the portions 17 of the body 1.

The portions 17 of the body 1 are brought together with a nut 49 inside which a tube 4 passes.

The handle 37 of the retention device is composed of two elastic arms 50 (FIG. 3) enclosed in a slot 51 of the portions 17 of the body 1.

The surgical suturing instrument of the present invention operates as follows.

The surgical suturing instrument proposed herein is aimed at establishing circular compression anastomoses in the hollow organs of the digestive tract by the end-to-end, end-to-side and side-to-side techniques. Considered below is an exemplary end-to-end anastomosis established in the anterior resection of the rectum.

After resection has been over purse-string sutures are applied to the rectal stump and the ends of the sigmoid colon. Then the instrument is introduced through the anal orifice into the rectum with the connecting ring 13 and the needle arrangement 5 brought together. Thereupon the nut 45 is rotated to advance the end of the rod 2 carrying the connecting ring 13 beyond the rectum, and the purse-string suture on the rectal stump is drawn tight. Next the end of the sigmoid colon is moved towards the end of the rod 2 carrying the connecting ring 13 and the purse-string suture on the sigmoid colon is drawn tight, whereupon the surplus threads of the purse-string sutures are cut off and the nut 45 is rotated to bring the connecting ring 13 and the needle arrangement 5 together till the suturing position is attained. Then the element 34 is rotated, by means of the handle 37 of the retention device until the recesses 35 and 36 coincide, that is, to unlock the hollow tube 4, whereupon the handle 14 is depressed so as to rotate round the hinge joint 15. As a result, the lever 18 interacts with the hollow tube 4 to cause it to move along with the knife 3 and the split bush 23 held thereto, which accommodates the retainer shaped as the hollow tube 25.

Figure 8:
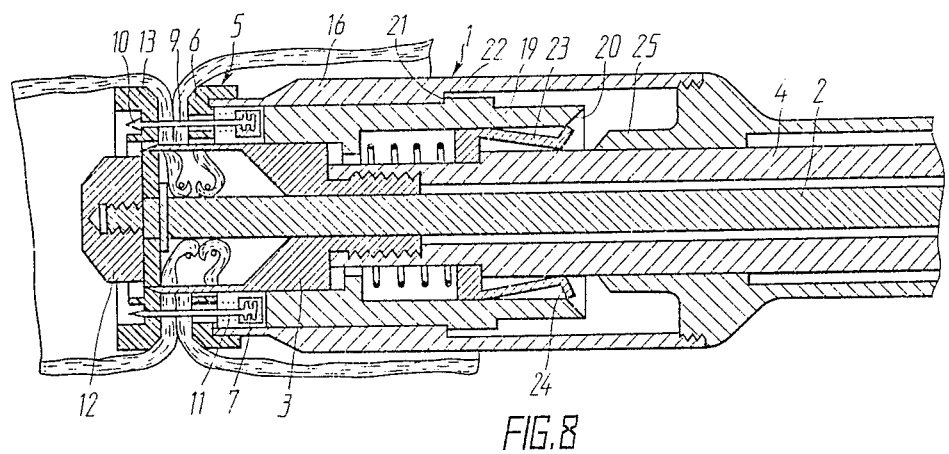
FIG. 8 is a longitudinal sectional view of the surgical suturing instrument while the connecting ring is being cut through, according to the invention.

The split bush 23 interacts, with its outside taper collar 24, with the hollow chamfer 20 of the pusher 19, causing it to travel along with the ring-shaped element 7 of the needle arrangement 5. The needles 9 pass through the holes 8 in the ring-shaped element 6 and pierce the tissues being sutured and the connecting ring 13, whereupon the needles 9 having the locking cones 10 are fixed in position in the ring 13. Then the retainer 25 rigidly coupled to the body 1 is located in the interior of the split bush 23, while the pusher 19 interacts through its stop 21 with the stop 22 of the body 1 and ceases travelling, thus exerting no pressure on the ring-shaped element 7 of the needle arrangement 5. Upon further advancement of the hollow tube 4 the bush 23 enters the interior of the pusher 19 (FIG. 8) without causing it to travel, while the knife 3 cuts through the tissues being sutured and establishes an opening in the connecting ring 13.

According to an alternative embodiment of the retainer of the split bush 23 (FIG. 5), travelling of the hollow tube 4 causes the rod 2 to interact, through its stop 30, with the supporting element 27 which is located in the diametral opening of the bush 26 and in the longitudinal slots 38 of the tube 4 so that the bush 26 remains stationary and is no longer located in the interior of the split bush 23, thereby unlocking it at the instant following the piercing of the connecting ring 13 by the needles 9 and fixing therein the needles 9 provided with the locking cones 10.

Figure 9:
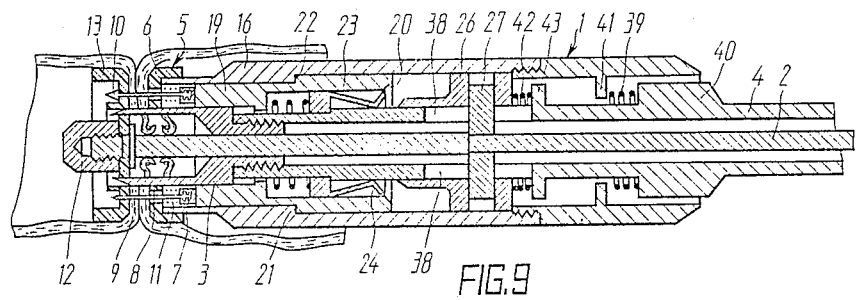
FIG. 9 shows the same as in FIG. 8 with reference to an alternative embodiment of the surgical suturing instrument.

Upon further advancing of the hollow tube 4 the bush 23 enters the interior of the pusher 19 without causing it to travel, while the knife 3 cuts off the surplus tissues and cuts through an opening in the connecting ring 13 (FIG. 9). Then the instrument is withdrawn from the rectum and the needle arrangement 5 and the connecting ring 13 remain in the rectal lumen and will afterwards (in 5 to 7 days) be discharged by the natural elimination way together with the necrotized tissues that has been compressed between the needle arrangement 5 and the connecting ring 13. By that day the rectal walls get united peripherally from the compression zone. Before the needle arrangement 5 and the connecting ring 13 are expelled the intestinal contents are free to pass through the opening cut by the cylindrical knife.

A total of 12 surgical procedures have been carried out on test dogs with the use of the surgical suturing instrument considered herein and 20 operations under clinical conditions on the stomach, small and large intestines.

A well-formed anastomosis free from cicatricial thickening was observed in the test animals operated upon.

In surgery on the stomach there were employed the rings of an appropriate diameter, which in all cases were freely discharged by the natural way of elimination. No postoperative morbid events were observed. The patients operated upon recovered 5 to 7 days earlier than the control patients due to a less degree of injury to the living tissues being sutured.

INDUSTRIAL APPLICABILITY

The invention can find application for surgery on the organs of the alimentary tract, predominantly on the intestines, stomach and esophagus.

We claim:

1. A surgical suturing instrument for establishing circular compression anastomoses in the organs of the digestive tract, comprising a needle arrangement (5) accommodated in a hollow body (1) and having a first ring-shaped element (6) with a plurality of holes (8), and a second ring-shaped element (7) coaxial with the first one and carrying a number of needles (9) fixed in position thereon, each of said needles corresponding to one of the holes (8) in the first ring-shaped element (6), while at least part of the needles have a locking cone (10) at the free end thereof; a rod (2) accommodated in the hollow body (1), said rod carrying at one of its ends a connecting ring (13) fixed stationary with the aid of a nut (12), the connecting ring being adapted for the needles (9) to pass through when establishing an anastomosis and those needles which have a locking cone (10) get secured in position in the connecting ring (13), a hollow cylindrical knife (3) having such an inside diameter that enables the nut (12) to pass freely therethrough, the knife being held to a hollow tube (4) which is arranged coaxially in the hollow body (1) and which accommodates the rod (2) located coaxially therewith, and a mechanical actuator of the hollow cylindrical knife (3) adapted to interact with the hollow tube (4), characterized in that it has a pusher (19) upon one of whose ends rests the second ring-shaped element (7) of the needle arrangement (5), while its other end has a hollow chamfer (20) and a stop (21) which is adapted to interact with a stop (22) of the hollow body (1) so as to restrict the travel of the second ring-shaped element (7) in the course of anastomosing, a split bush (23) fitted on the hollow tube (4) and having an outside taper collar (24) adapted to engage the hollow chamfer (20) of the pusher (19) and a retainer (25) of the split bush (23) located on the hollow tube (4) inside the split bush (23).

2. A surgical suturing instrument as claimed in claim 1, characterized in that in order to ensure against spontaneous travel of the pusher (19) provision is made for a retention device comprising a cylinder-shaped element (34) which has a recess (35) and is located inside the hollow body (1) close to the hollow tube (4) in which a cylindrical recess (36) is made, corresponding to the cylinder-shaped element (34), and a handle (37) provided on the cylinder-shaped element (34) rotatably with respect to the hollow body (1) in order to bring the recess (35) in the cylinder-shaped element (34) in coincidence with the cylindrical recess (36) of the hollow tube (4), thus letting the hollow tube (4) move and preparing the instrument for suturing.

3. A surgical suturing instrument as claimed in claim 1 or 2, characterized in that the retainer of the split bush (23) is shaped as a hollow tube (25) rigidly coupled to the hollow body (1) and arranged coaxially therewith.

4. A surgical suturing instrument as claimed in claim 3, characterized in that the hollow tube (25) which is in fact the retainer of the split bush (23) serves as the casing of the instrument and has a length comparable with the length of the rod (2).

5. A surgical suturing instrument as claimed in claim 1 or 2, characterized in that the retainer of the split bush (23) comprises a bush (26) coaxial with the rod (2) and having a diametral opening (28), and a supporting element (27) located in the diametral opening (28) of the bush (26) and having its own opening (29) coaxial with the bush (26) and adapted for the rod (2) to pass, the rod having a stop (30) adapted to interact with the supporting element (27) so as to stop the pusher (19) and hence the needle arrangement (5) at the instant when the hollow cylindrical knife (3) cuts through the connecting ring (13).

6. A surgical suturing instrument as claimed in claim 5, characterized in that the hollow tube (4) on which the hollow cylindrical knife (3) is secured, is provided with longitudinal slots (38) located on its portion interacting with the bush (26) of the retainer of the split bush (23), which slots are adapted for the supporting element (27) to slide with respect to the hollow tube (4) in the course of anastomosing.

7. A surgical suturing instrument as claimed in claim 5, characterized in that the hollow tube (4) carrying the hollow cylindrical knife (3) is in fact the casing of the instrument and has a length comparable with the length of the rod (2).

8. A surgical suturing instrument as claimed in claim 6, characterized in that the hollow tube (4) carrying the hollow cylindrical knife (3) is in fact the casing of the instrument and has a length comparable with the length of the rod (2).

9. A surgical suturing instrument as claimed in claim 5, characterized in that the hollow body (1) is spring-actuated with respect to the hollow tube (4) carrying the hollow cylindrical knife (3) and is adapted to interact with the bush (26) of the retainer of the split bush (23) thus contributing to less overcompression of the tissues being sutured should these be of considerable thickness.

10. A surgical suturing instrument as claimed in claim 6, characterized in that the hollow body (1) is spring-actuated with respect to the hollow tube (4) carrying the hollow cylindrical knife (3) and is adapted to interact with the bush (26) of the retainer of the split bush (23) thus contributing to less overcompression of the tissues being sutured should these be of considerable thickness.

11. A surgical suturing instrument as claimed in claim 7, characterized in that the hollow body (1) is spring-actuated with respect to the hollow tube (4) carrying the hollow cylindrical knife (3) and is adapted to interact with the bush (26) of the retainer of the split bush (23) thus contributing to less overcompression of the tissues being sutured should these be considerable thickness.

12. A surgical suturing instrument as claimed in claim 5, characterized in that the bush (26) of the retainer of the split bush (23) is spring-actuated with respect to the hollow tube (4) on which the hollow cylindrical knife (3) is made fast.

13. A surgical suturing instrument as claimed in claim 9, characterized in that the bush (26) of the retainer of the split bush (23) is spring-actuated with respect to the hollow tube (4) on which the hollow cylindrical knife (3) is made fast.

* * * * *